United States Patent
Vaisburd et al.

(10) Patent No.: US 8,447,560 B2
(45) Date of Patent: May 21, 2013

(54) APPARATUS AND METHOD FOR IDENTIFYING THE ABSOLUTE ROTATION OF A ROTATING IMAGING SYSTEM

(75) Inventors: Alexander Vaisburd, Haifa (IL); Leonid Yakubovsky, Haifa (IL)

(73) Assignee: General Electric Company, Schenectady, NY (US)

( * ) Notice: Subject to any disclaimer, the term of this patent is extended or adjusted under 35 U.S.C. 154(b) by 426 days.

(21) Appl. No.: 12/270,575

(22) Filed: Nov. 13, 2008

(65) Prior Publication Data
US 2010/0121604 A1    May 13, 2010

(51) Int. Cl.
*G01C 9/00*    (2006.01)

(52) U.S. Cl.
USPC .......................................... 702/151

(58) Field of Classification Search
USPC .......................................... 702/151
See application file for complete search history.

(56) References Cited

U.S. PATENT DOCUMENTS

| | | | |
|---|---|---|---|
| 2,406,211 A | 8/1946 | Flint | |
| 2,738,491 A | 3/1956 | Mihalakis | |
| 3,289,475 A | 12/1966 | Kenyon | |
| 4,366,577 A * | 12/1982 | Brandt | 378/194 |
| 4,740,690 A * | 4/1988 | Mosier | 250/231.18 |
| 5,523,571 A | 6/1996 | Velazquez et al. | |
| 6,097,030 A | 8/2000 | Tokarski et al. | |
| 7,573,034 B2 | 8/2009 | Heath et al. | |
| 2003/0160731 A1* | 8/2003 | Wensink | 343/892 |
| 2003/0177649 A1* | 9/2003 | Ito et al. | 33/1 PT |
| 2005/0259782 A1* | 11/2005 | Kasuya | 378/15 |
| 2006/0120513 A1 | 6/2006 | Buttner et al. | |
| 2006/0202650 A1* | 9/2006 | Hausner et al. | 318/268 |
| 2006/0241408 A1 | 10/2006 | Yakubovsky et al. | |
| 2006/0285641 A1* | 12/2006 | Scherch | 378/65 |
| 2007/0183566 A1* | 8/2007 | Tsujita et al. | 378/37 |
| 2008/0267352 A1* | 10/2008 | Aoi et al. | 378/65 |
| 2010/0119043 A1 | 5/2010 | Yakubovsky | |

OTHER PUBLICATIONS

E-Chain product overview, http://www.igus.com/echain.asp, igus inc.—E-Chain cable carrier for automated machinery, (7) pages.
LeviChain Energy Chain Systems, LeviChain—magnetically suspended cable carrier, http://www.igus.com/levichain.asp, (2) pages.
Energy Chain Systems "Zipper"—Zipper Chain for fast installation, http://www/igus.com/show_zip2.asp, (3) pages.
Data Sheet for Bourns 3590—Precision Potentiometer, RoHS Directive 2002/95/EC Jan. 27 2003 including Annex, (2) pages.
Technical Data Sheet for Tilt sensor example, Freescale Semiconductor, Inc., Document Number: MMA7450L, Rev. 2, Jul. 2007, (1) page.

* cited by examiner

*Primary Examiner* — Stephen Cherry
(74) *Attorney, Agent, or Firm* — The Small Patent Law Group; Dean D. Small

(57) ABSTRACT

A rotating imaging system has a rotating portion, an idler, at least one sensor, a tilt sensor and a processor. The rotating portion has a diameter and rotates about a central axis. The idler rotates about an axis parallel to the central axis, and has a second diameter that is smaller than the diameter of the rotating portion. The rotating portion and the idler engage with each other such that both rotate simultaneously. The at least one sensor detects flags on the idler as the idler rotates. The tilt sensor is mounted to the rotating portion and determines a rotation angle of the rotating portion within a range of one revolution, and the processor determines an absolute rotation of the rotating portion based on at least a signal from the at least one sensor and the rotation angle determined by the tilt sensor.

21 Claims, 8 Drawing Sheets

Rear View    Front View

APPARATUS AND METHOD FOR IDENTIFYING THE ABSOLUTE ROTATION OF A ROTATING IMAGING SYSTEM

BACKGROUND OF THE INVENTION

This invention relates generally to imaging systems, and more particularly to imaging systems that use a retractor.

Some imaging systems such as nuclear medicine imaging systems having gamma cameras use a retractor as a transmission system to transmit power, signals and data between the imaging detectors and electronics used for processing, control and power. The retractor may also be referred to as a cable guidance system and allows a limited rotation span. For example, the rotor or rotating portion upon which the imaging detectors are mounted typically may be rotated more than one, but less than two full rotations in one or both of the clockwise (CW) and counter-clockwise (CCW) directions from a zero position. In contrast, a slip ring, such as those used by computed tomography (CT) and some gamma camera systems, allow unlimited rotations in both the CW and CCW directions.

Electronics track the rotating portion during normal use, such as by receiving rotation input from an absolute encoder, potentiometer, tooth wheel and flag and/or encoder combination, and the like. An angular read-out on a display and/or a warning when nearing the end of travel may be provided. End of travel microswitches have also been used to try to prevent the system from reaching or exceeding a travel limit. Mechanical devices such as hard stops have been used, but cannot safely stop heavy modern imaging detectors and may not be easily positioned to stop rotation at a position less than two full revolutions. If the tracking or corresponding display fails, such as during a power outage or computer or other component malfunction, an operator may not know if the retractor is nearing the end of travel. Moving the rotating portion beyond the end of travel, such as manually or by driving with a motor, may cause severe damage to the system. Specifically, the retractor may be damaged if the rotating portion travels beyond the designed travel limit.

BRIEF DESCRIPTION OF THE INVENTION

In one embodiment, a rotating imaging system has a rotating portion, an idler, at least one sensor, a tilt sensor and a processor. The rotating portion has a diameter and is configured to rotate about a central axis. The idler is configured to rotate about an axis parallel to the central axis, and has a second diameter that is smaller than the diameter of the rotating portion. The rotating portion and the idler are configured to engage with each other such that both rotate simultaneously. The at least one sensor is configured to detect flags on the idler as the idler rotates. The tilt sensor is mounted to the rotating portion and is configured to determine a rotation angle of the rotating portion within a range of one revolution, and the processor is configured to determine an absolute rotation of the rotating portion based on at least a signal from the at least one sensor and the rotation angle determined by the tilt sensor.

In another embodiment, a method for determining an absolute rotation of a rotating portion within an imaging system comprises rotating a rotating portion and an idler simultaneously without slippage. The rotating portion and the idler are configured to have a non-integer ratio of rotation with respect to each other. A flag is detected on the idler, and a rotation angle of the rotating portion coinciding with the detection of the flag is detected. An absolute rotation of the rotating portion is determined based on the detection of the flag and the rotation angle.

In yet another embodiment, a rotating imaging system comprises a rotating portion configured to rotate about a central axis and an idler configured to rotate about an axis parallel to the central axis. The rotating portion and the idler are configured to engage with each other such that both rotate simultaneously without slippage, and the idler and the rotating portion have a non-integer ratio of rotation with respect to each other. At least one sensor is configured to detect flags on the idler as the idler rotates, and a tilt sensor is mounted to the rotating portion and is configured to determine a rotation angle of the rotating portion. A processor is configured to determine an absolute rotation of the rotating portion based on a signal from the at least one sensor and the rotation angle coinciding with the detection of the flag.

DETAILED DESCRIPTION OF THE INVENTION

Figure 1:
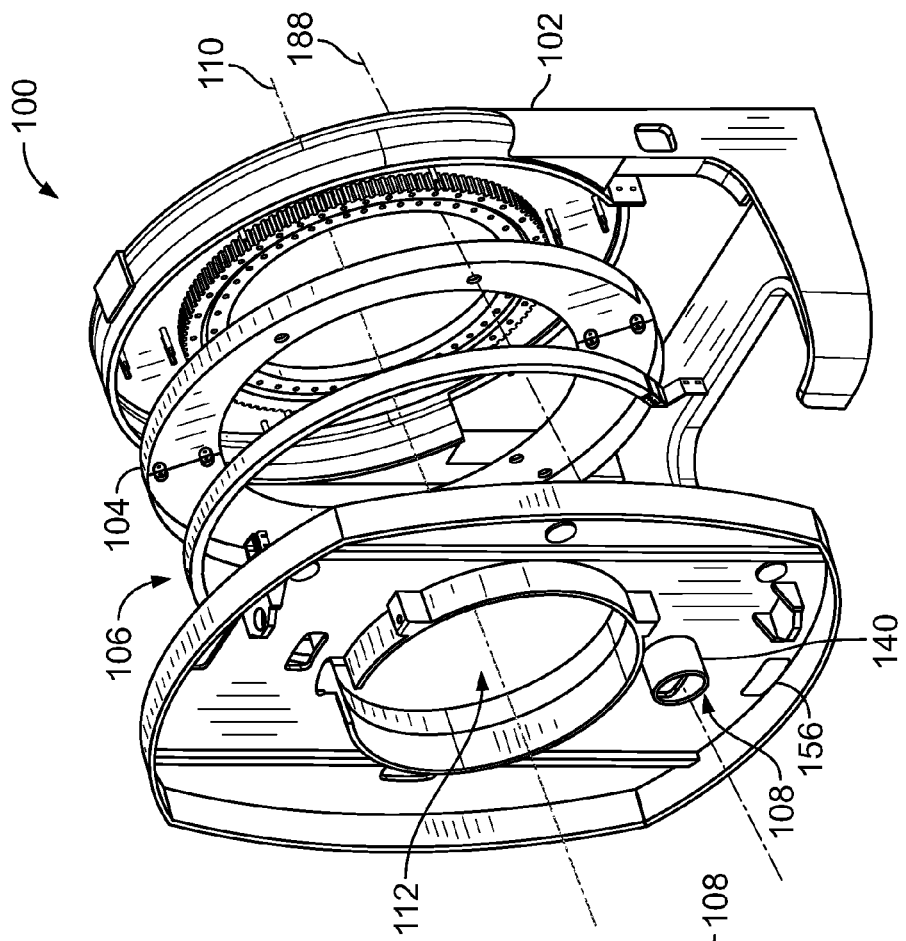
FIG. 1 illustrates exploded rear and front views of a gantry that may be used within a rotating imaging system formed in accordance with an embodiment of the present invention.
Figure 1:
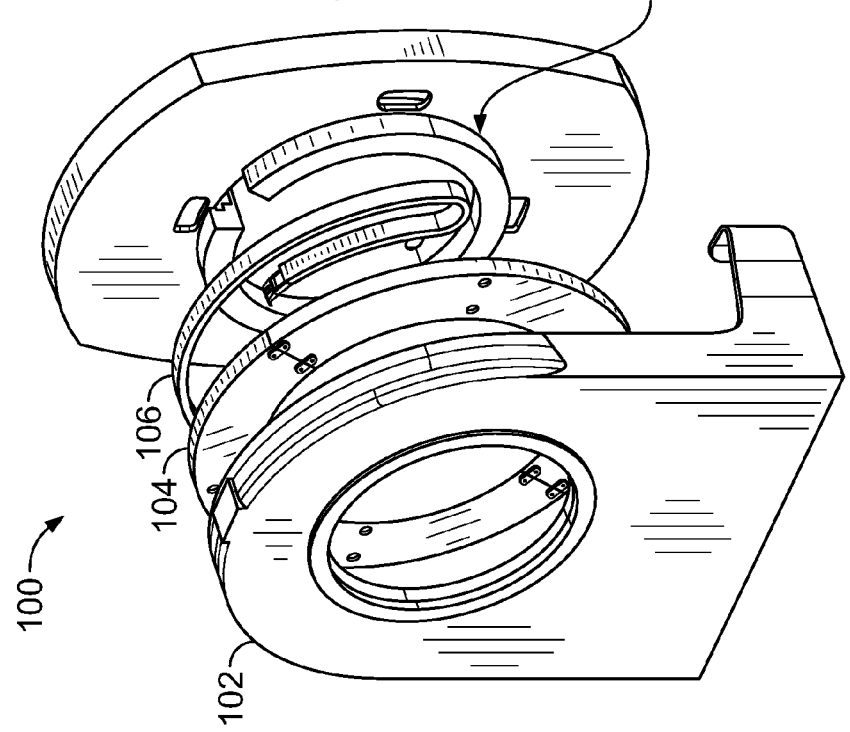

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

FIG. 1 illustrates exploded rear and front views of a gantry 100 that may be used within a rotating imaging system. A stator 102 is fixed to the floor or other structure, such as one or more rails (not shown). A rotor or rotating portion 108 is attached to and/or supported by the stator 102 such as through a slew bearing (not shown). A smaller wheel, also referred to as an idler 140, is fixed to the stator 102 or other non-rotating structure and is mated with the rotating portion 108 such that both the idler 140 and the rotating portion 108 rotate simultaneously without slippage. A tilt sensor 156 is mounted to, and rotates with, the rotating portion 108. The tilt sensor 156 detects the angular position or rotation angle of the rotating portion. In one embodiment, the tilt sensor 156 may be configured to detect angular rotations that are less than one degree.

A retractor cage 104 is fixed to the stator 102 and is configured to hold a retractor 106. The retractor 106 moves within the retractor cage 104 when the rotating portion 108 rotates. However, the retractor cage 104 is static and does not rotate.

The retractor 106 is a signal and power transmission system having a coiled transmission line that winds and unwinds as the rotating portion 108 rotates about a central axis 110 extending through an opening 112. The opening 112 is large enough to accommodate, for example, a patient on a pallet of a table (all not shown). As the rotating portion 108 rotates, the idler 140 simultaneously rotates about axis 188 that is parallel to the central axis 110. The retractor 106 conveys at least one of power, image, data, and control signals between gamma camera imaging detector(s) (not shown) and a computer or other processor (not shown). In general, the retractor 106 may be capable of rotating about the central axis 110 for less than two full revolutions, thus having a rotation span or operating range of less than 720 degrees. In one embodiment, the retractor 106 rotates approximately one and a half revolutions in one direction, or about 540 degrees. In another embodiment, the retractor 106 may rotate more or less than one and a half revolutions in one direction while rotating less than one revolution in the opposite direction. In yet another embodiment, the retractor 106 may rotate more than two revolutions in at least one of the directions.

Figure 2:
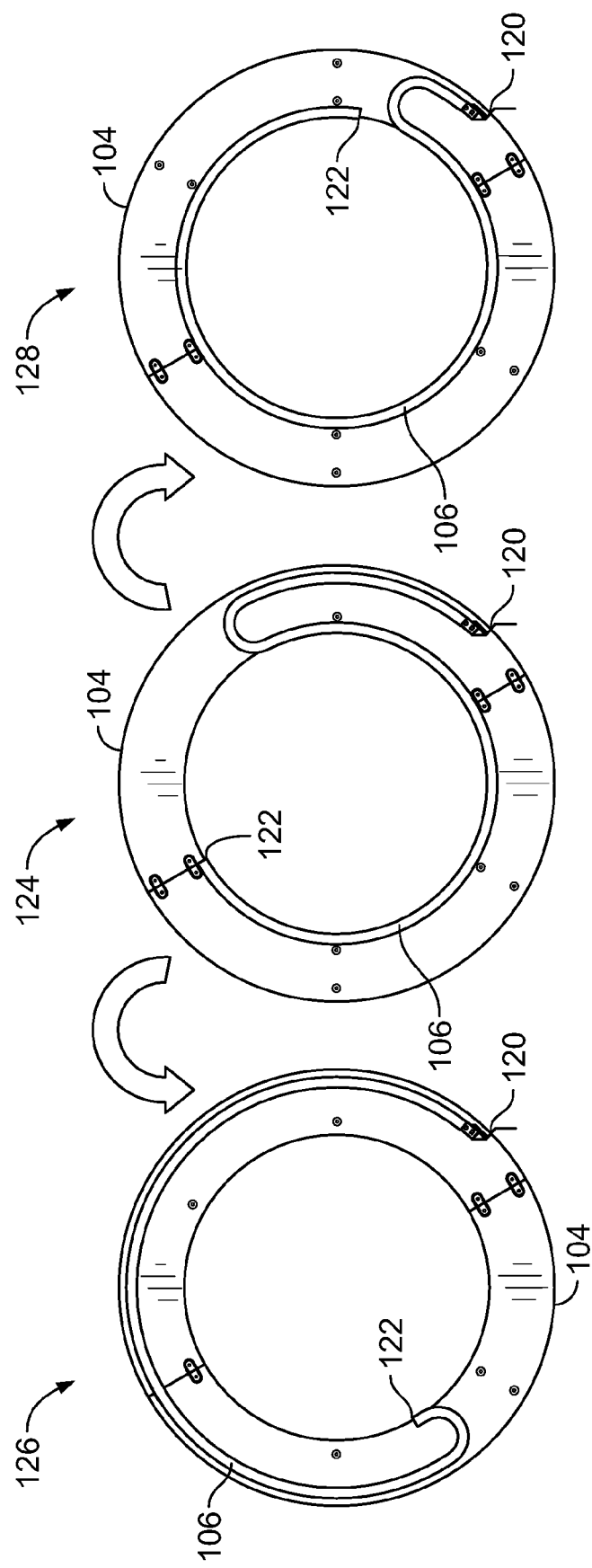
FIG. 2 illustrates an exemplary path of a retractor within a retractor cage as the rotating portion (shown in FIG. 1) is rotated in accordance with an embodiment of the present invention.

FIG. 2 illustrates an exemplary path of the retractor 106 within the retractor cage 104 as the rotating portion 108 (shown in FIG. 1) is rotated. The retractor 106 has a fixed or static end 120 attached to the retractor cage 104. Cables or other circuitry (not shown) may be interconnected at the static end 120 to convey signals between the retractor 106 and a processor, motion controller and/or other circuitry (not shown). A moving end 122 is not fixed to the retractor cage 104 and indicates the position of the retractor 106 as the retractor 106 is rotated. The position of the moving end 122 depends on the amount of clockwise (CW) or counter-clockwise (CCW) rotation. Cables or other circuitry (not shown) convey signals between the moving end 122 of the retractor 106 and the gamma camera imaging detector(s).

The retractor 106 may be coiled and/or folded within the retractor cage 104 at a zero degree position 124. The retractor 106 is also shown in a 450 degree CCW position 126. In this example, the maximum rotation in the CCW direction is 450 degrees. If the retractor 106 is rotated further than 450 degrees in the CCW direction, damage to the retractor 106 and/or other components may result. The 450 degree rotation is slightly less than one and a half full rotations in the CCW direction. However, it should be understood that the retractor 106 may be configured to rotate more or less than 450 degrees in the CCW direction.

The retractor 106 is further shown in a 130 degree CW position 128. In this example, the maximum rotation in the CW direction is 130 degrees, and if the retractor 106 is rotated further in the CW direction, damage to the retractor 106 may result. As with the CCW direction, the retractor 106 may be configured to rotate greater or lesser distances than 130 degrees in the CW direction.

In the illustrated embodiment, the total maximum rotation range of the retractor 106 is 580 degrees. However, the maximum rotation range may be greater than 720 degrees to allow at least two full revolutions in either the CW or CCW direction. In another embodiment, the retractor 106 may be configured to rotate further in the CW direction, such as 450 degrees, while rotating less than one full rotation in the CCW direction. In yet another embodiment, the retractor 106 may be configured to rotate approximately one full rotation in both CW and CCW directions.

Figure 3:
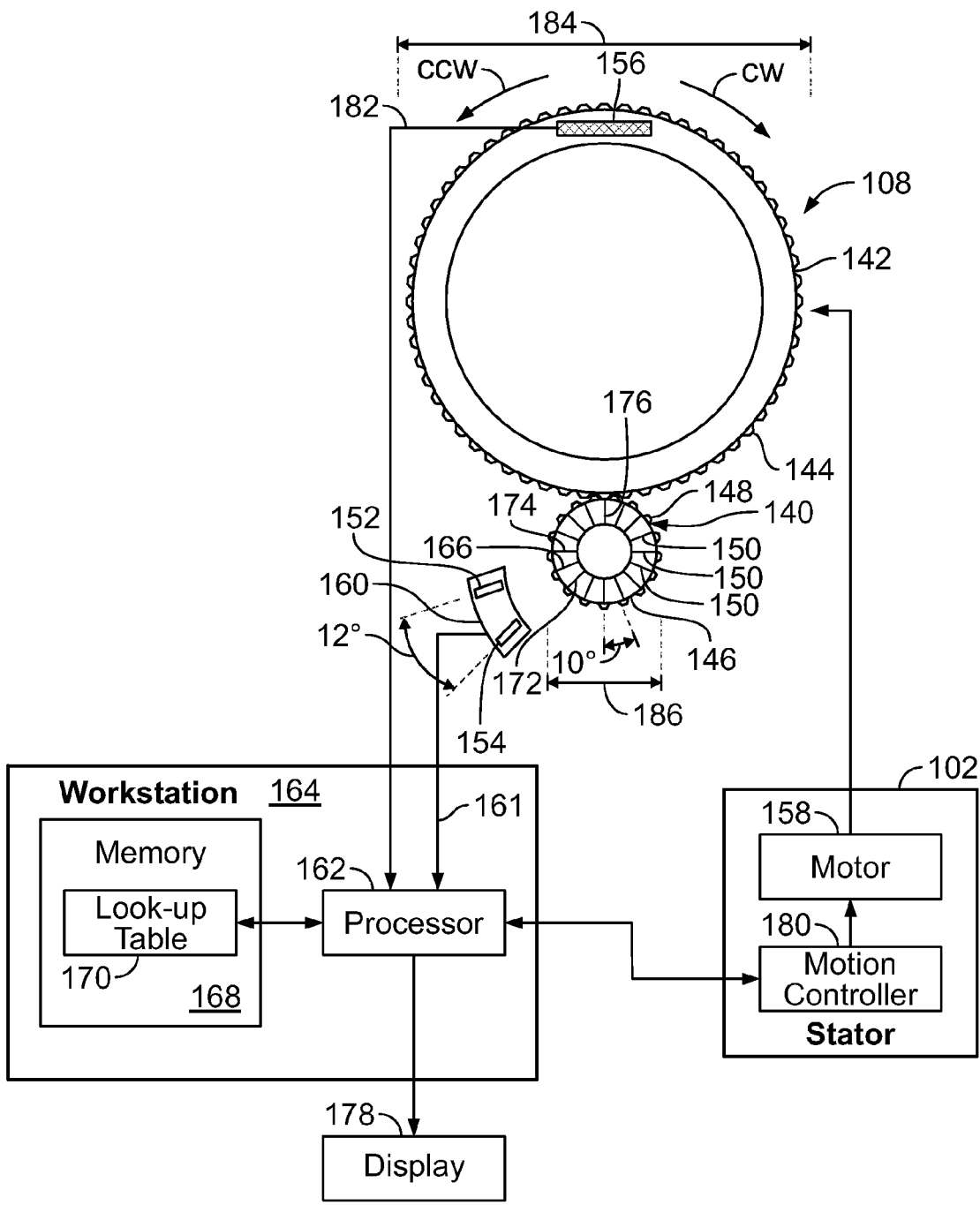
FIG. 3 illustrates the rotating portion configured to rotate simultaneously with a smaller wheel or idler in accordance with an embodiment of the present invention.

FIG. 3 illustrates a wheel, such as the rotating portion 108, configured to rotate simultaneously with a smaller wheel, herein referred to as an idler 140. The rotating portion 108 has an outer edge 142 with teeth 144 extending outwardly from the outer edge 142. The teeth 144 are evenly distributed along the entire outer edge 142. The idler 140 also has teeth 148 extending outwardly from an outer edge 146. Again, the teeth 148 are evenly distributed along the entire outer edge 146. The teeth 144 of the rotating portion 108 engage with the teeth 148 of the idler 140 so that when a motor 158 rotates the rotating portion 108, the idler 140 also rotates. No slippage is allowed between the rotating portion 108 and the idler 140. The motor 158 may be controlled by a motion controller 180, both of which may be housed within the stator 102.

The rotating portion 108 has a diameter 184 that is larger than a diameter 186 of the idler 140. When the rotating portion 108 rotates one full rotation, the idler 140 rotates more than one full rotation, and there is a non-integer ratio of rotation between the rotating portion 108 and the idler 140. For example, if the idler 140 is ten percent smaller than the rotating portion 108, when the rotating portion 108 rotates one full rotation, the idler 140 rotates one full rotation plus ten percent. If the rotating portion 108 rotates another full rotation in the same direction, the final position of the idler 140 would be two full rotations plus 20 percent with respect to the zero position.

In one embodiment, the rotating portion 108 has 234 teeth 144 and the idler 140 has 59 teeth 148. Therefore, for every full rotation of the rotating portion 108, the idler 140 rotates approximately twelve degrees less than four complete turns (e.g. approximately 12.203 degrees). In this example, the ratio of rotation between the rotating portion 108 and the idler 140 is the non-integer ratio of 3.9661. It should be understood that other non-integer ratios may be used, as well as different numbers of teeth 144 and 148 and sizes of the idler 140. For example, the idler 140 may be made smaller such that less room within the stator 102 may be needed.

The idler 140 has a plurality of flags 150 that are spaced equidistant around the idler 140. In one embodiment, 36 flags 150 may be positioned ten degrees apart from each other. It should be noted that less than 36 flags 150 are shown for clarity. It should be understood that more or less flags may be used, while still positioning the flags equidistant from each other. In other embodiments, the flags 150 may be spaced or positioned such that not every flag 150 is equidistant with respect to the nearest neighboring flags 150. Individual flags 166, 172, 174 and 176 are referenced below and thus have been given different item numbers for clarity. The flag 176, when positioned at the top center position of the idler 140, indicates the zero degree position 124 (shown in FIG. 2) of the rotating portion 108.

At least one sensor 152 and 154 (two sensors are shown) is mounted to structure (not shown) within the stator 102 proximate to the idler 140. (The sensors 152 and 154 are shown separate from the idler 140 for clarity.) In other embodiments, a single sensor may be used or more than two sensors may be used. The sensors 152 and 154 may be provided within a sensor assembly 160 that transmits signals from, and provides power to, the sensors 152 and 154. The sensors 152 and 154 are fixed and thus do not move as the rotating portion 108 and the idler 140 rotate. The sensors 152 and 154 detect each of the flags 150 when the flags 150 pass the sensors 152 and 154 and/or are within a predetermined distance of the sensors 152 and 154.

In one embodiment, the sensors 152 and 154 are positioned twelve degrees apart from each other. When the rotating portion 108 and the idler 140 are at the zero degree position 124, the sensors 152 and 154 may be positioned equidistant on either side of one of the flags 150, such as the flag 166. Therefore, the sensor 152 is positioned six degrees to one side of the flag 166 and the sensor 154 is positioned six degrees to the other side of the flag 166. It should be understood that the sensors 152 and 154 may be positioned a different number of degrees apart and with different orientation to the flag 166 or to other flags 150. In the illustrated embodiment, because the sensors 152 and 154 are positioned twelve degrees apart with respect to each other and the flags 150 are positioned ten degrees apart with respect to each other, only one of the sensors 152 or 154 will detect a flag 150 at any one time. In other embodiments, the sensors 152 and 154 and flags 150 may be positioned such that more than one flag 150 may be simultaneously detected.

Figure 4:
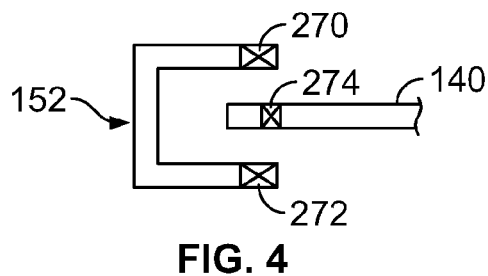
FIG. 4 illustrates a sensor formed in accordance with an embodiment of the present invention for detecting flags on the idler (shown in FIG. 3).

The flags 150 are physical structures to be detected by the sensors 152 and 154. In one embodiment, as illustrated in FIG. 4, the sensor 152 is an optocoupler that pairs a light source such as a light emitting photo-diode (LED) 270 with a photosensitive detector 272. The flags 150 are holes 274 that are formed (e.g. drilled) through the idler 140. If the sensors 152 and 154 are optocouplers, the idler 140 would block the light transmission most of the time. The flag 150 is thus detected when the photosensitive detector 272 detects the light of the LED 270 through the hole 274.

In another embodiment, the flags 150 may be teeth, veins or other protrusions that extend outwardly from a surface of the idler 140 and the sensors 152 and 154 may be optocouplers. The flags 150 may be positioned to interfere with or block the light detected by the photosensitive detector 272 when aligned with the sensor 152 or 154. In yet another embodiment, the flag 150 may be a small magnet and the sensors 152 and 154 may be magnetic field sensors wherein a metal reed or other metal component may be pulled to a contact when the flag 150 passes within a predetermined area of the sensor 152 or 154. In still other embodiments, the sensors 152 and 154 may be ultrasound-based sensors that may be paired with flags 150 formed as protrusions, or any other sensor that detects the presence and absence of the flag 150 based on an ultrasonic response within a small predetermined area.

Returning to FIG. 3, the sensor assembly 160 and/or the sensors 152 and 154 transmit signals to a processor 162 as indicated by line 161. The transmission may be wired or wireless. In one embodiment, the line 161 may be formed within the retractor 106. The processor 162 may be within a workstation 164 positioned near the rotating portion 108. Alternatively, the processor 162 may be housed within the stator 102. When either of the sensors 152 or 154 detects a flag 150, the applicable sensor 152, 154 or the sensor assembly 160 transmits an indication, such as a pulse, to the processor 162. In another embodiment, rather than providing an indication when the state changes, the sensors 152 and 154 may repeatedly or constantly transmit an indication of the current status or state to the processor 162.

The tilt sensor 156 is mounted on the rotating portion 108 and may or may not be visible to the operator. For example, the tilt sensor 156 may be mounted inside a cover that conceals the rotating portion 108. The tilt sensor 156 measures tilt or rotation angles up to 360 degrees. Therefore, the tilt sensor 156 can determine the angular position or rotation angle of the rotating portion 108 with respect to the zero degree position 124, but cannot identify that a complete revolution has been accomplished in one direction and that the rotation angle is associated with a second rotation. Thus, the output of the tilt sensor 156 may not be the absolute rotation of the rotating portion 108, which may be greater than 360 degrees. The tilt sensor 156 continuously transmits the current rotation angle to the processor 162 as indicated by line 182. The transmission may be hardwired or wireless. Optionally, the tilt sensor 156 may only transmit the current rotation angle when the tilt sensor 156 senses a change in the rotation angle, such as when the rotating portion 108 is being rotated.

A memory 168 stores a look-up table 170 that correlates the reading (e.g. sensed tilt angle) from the tilt sensor 156 and a corresponding indication from one of the sensors 152 and 154 with an absolute rotation of the rotating portion 108. For example, the memory 168 may be a non-volatile memory or may be reloaded upon power-up of the workstation 164. It should be understood that other storage means and formats may be used.

Throughout the allowed rotation span, for each rotation angle of the rotating portion 108 that is associated with the simultaneous detection of a flag 150, the table 170 stores a correlated absolute rotation. Continuing the above example, for the first CCW revolution of the rotating portion 108, the four rotation angles that are coincident with the sensor 152 detecting the flag 166 are correlated with four different absolute rotations and the three rotation angles that are coincident with the sensor 154 detecting the flag 166 are correlated with three different absolute rotations. After one CCW revolution of the rotating portion 108, the idler 140 is offset by approximately twelve degrees because the idler 140 rotates CW slightly less than four full revolutions (a non-integer ratio). Therefore, during the second CCW revolution of the rotating portion 108, the table 170 correlates the eight rotation angles that are coincident with the detection of the flag 166 by the sensors 152 and 154 with eight absolute rotations that are different with respect to each other and different with respect to the absolute rotations associated with the first CCW revolution.

Figure 5:
FIG. 5 illustrates an exemplary look-up table correlating rotation angles of the rotating portion with absolute rotations in accordance with an embodiment of the present invention.

FIG. 5 illustrates an exemplary look-up table 170. Although only a few exemplary rotation angles are illustrated in column 190, it should be understood that many more rotation angles are correlated with absolute rotations in column 196 in both the positive and negative rotation directions. In this example, positive and negative rotations are associated with CW and CCW rotations, respectively, of the rotating portion 108. A technical effect of at least one embodiment is the ability to determine the absolute rotation of the rotating portion 108 based on input from the tilt sensor 156 and at least one of the sensors 152 and 154. When the processor 162 receives an indication or pulse from one of the sensors 152 or 154, provided in a sensor one column 192 and sensor two column 194, respectively, the processor 162 correlates the indication with the rotation angle in column 190 that coincides with the detection of the flag 150. In other words, when the flag 150 is detected, the processor 162 determines what sensor 152 or 154 provided the indication and the rotation angle that is received simultaneously or substantially simultaneously from the tilt sensor 156. The processor 162 thus determines from the table 170 the absolute rotation in column 196.

In one embodiment, if a single sensor 152 or 154 is used, the table 170 may include only the rotation angle and absolute rotation associated with the single sensor. If additional sensors (not shown) are used, the table 170 will include additional rotation angles and absolute rotations associated with any additional sensor and/or combinations of sensors.

Returning to FIG. 3, if the rotating portion 108 is rotated CCW from the zero degree position 124, the idler 140 rotates CW. The first flag 150 that is sensed is the flag 172, which is sensed by sensor 154 after the idler 140 rotates four degrees. The sensor 154 transmits a signal to the processor 162 indicating that a flag 150 has been detected. The tilt sensor 156 simultaneously has been transmitting the current rotation angle of the rotating portion 108. By way of example only, the current rotation angle of the rotating portion 108 may be negative two degrees. The processor 162 accesses the look-up table 170 to determine the absolute rotation in column 196 based on both the rotation angle in column 190 from the tilt sensor 156 and the sensor 154, which in this example is negative two degrees. The processor 162 may display the absolute rotation on a display 178 that may be positioned near the stator 102 and/or the workstation 164.

As the rotating portion 108 is further rotated CCW, and the idler rotates CW by another two degrees, the sensor 152 detects the flag 166. The tilt sensor 156 transmits the current rotation angle of the rotating portion 108, which may be negative 2.5 degrees. The processor 162 accesses the look-up table 170 to determine the absolute rotation in column 196 based on both the rotation angle in column 190 from the tilt sensor 156 and the sensor 152, which in this example is negative 2.5 degrees. In one embodiment, if it is desired that smaller angular increments be detected, more flags 150 may be used with less than ten degrees of separation between neighboring flags 150.

Figure 6:
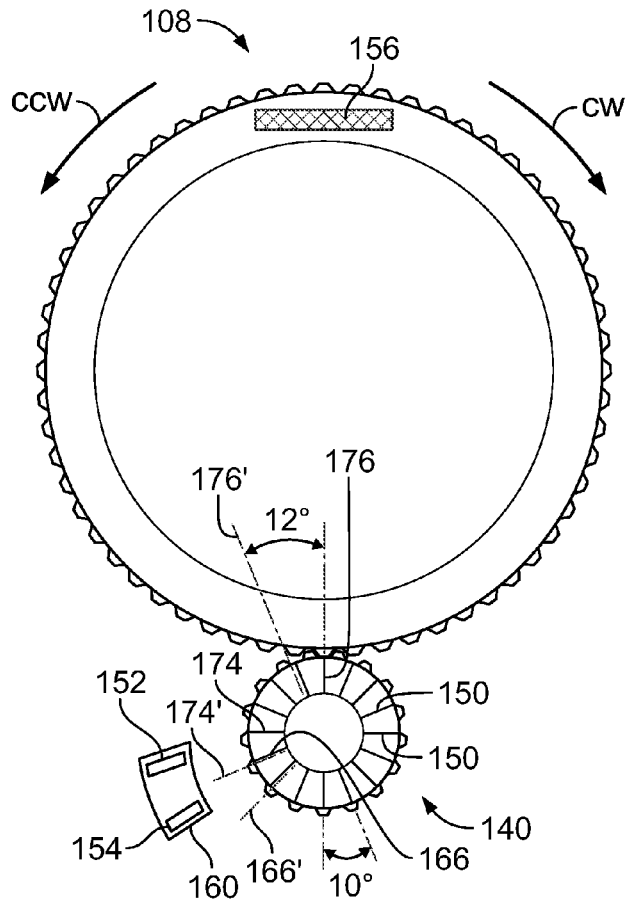
FIG. 6 illustrates the rotating portion rotated a full rotation counter-clockwise in accordance with an embodiment of the present invention.

FIG. 6 illustrates the rotating portion 108 rotated a full revolution CCW. The idler 140 has been rotated a non-integer number N of revolutions CW as discussed above. For example, after a full revolution of the rotating portion 108, the idler 140 is rotated approximately twelve degrees less than four full revolutions. Therefore, the flag 176 is now positioned twelve degrees from the zero degree position 124 and indicated as flag 176'. In addition, the flag 166 is now positioned six degrees to the other side of the sensor 154 and is shown as flag 166'. The flag 174 is now positioned eight degrees to the other side of the sensor 152 and is shown as flag 174'.

As the rotating portion 108 is further rotated CCW, the sensor 154 detects flag 166' after the idler 140 rotates six degrees. The tilt sensor 156 simultaneously has been transmitting the current rotation angle of the rotating portion 108, which in this example is negative 2.5 degrees. The processor 162 accesses the look-up table 170 to determine the absolute rotation in column 196 based on both the rotation angle in column 190 and the sensor 154. The combination of the pulse from the sensor 154 and the rotation angle of negative 2.5 degrees indicates that a full rotation has occurred and that the absolute rotation in column 196 is negative 360 degrees plus negative 2.5 degrees, or negative 362.5 degrees. In contrast, referring to the example above, the combination of the pulse from the sensor 152 and the angular rotation of negative 2.5 degrees indicated an absolute rotation in column 196 of negative 2.5 degrees. The processor 162 may display the absolute rotation in column 196 on the display 178 and may also display the number of rotations or revolutions, which in this example is one revolution in the CCW direction.

As the rotating portion 108 is further rotated CCW, the sensor 152 detects flag 174' after the idler 140 rotates an additional two degrees. The tilt sensor 156 transmits the current rotation angle in column 190 of the rotating portion 108, which may be negative three degrees. The processor 162 accesses the look-up table 170 to determine the absolute rotation based on both the rotation angle in column 190 and the sensor 152.

As the absolute rotation nears a designed end of travel, such as within a predetermined amount or distance of the end of travel in either direction, the processor 162 may display a warning on the display 178. The warning may be a message, a graphic or other indication and may be shown as a predetermined color, flashing or other display to draw the attention of the operator. Alternatively, the warning may be a sound or noise that is generated by the processor 162 to alert the operator. The processor 162 may also control the motion controller 180 to prevent further motion in the prohibited direction to prevent damage to the retractor 106. In one embodiment, when a warning condition is detected, the processor 162 may prevent motorized motion in the dangerous direction by sending an instruction to the motion controller 180. In some embodiments, when the processor 162 detects an approach to the travel limit, all automatic motions may be disabled and a manual recovery is needed. In other embodiments, an additional physical braking system (not shown) may be activated when a warning condition is detected. In yet other embodiments, power to the motor 158 may be removed when a warning condition is detected.

In the event that power has been lost and the absolute rotation is not known, the operator may easily determine the absolute rotation by moving the rotating portion 108 slowly in the CW or CCW direction. In one embodiment, a flag 150 is detected within four degrees rotation of the idler 140. The sensor 152 or 154 sends a signal to the processor 162. The tilt sensor 156 is continuously transmitting the rotation angle to the processor 162 or transmits the rotation angle when rotation of the rotating portion 108 is detected. The processor 162 identifies the sensor 152 or 154 that transmitted the signal and the rotation angle from the tilt sensor 156 and accesses the look-up table 170 to determine the absolute rotation in column 196. The processor 162 displays the absolute rotation on the display 178, along with the number of rotations or revolutions, the direction of rotation, and/or a warning of the end of travel, if applicable.

Figure 7:
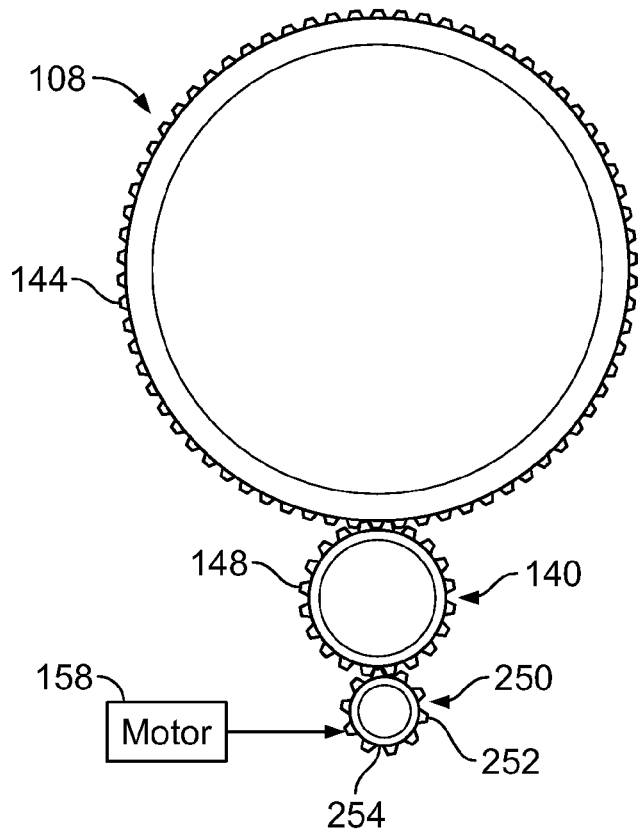
FIG. 7 illustrates another embodiment wherein an output from a motor drives the idler in accordance with an embodiment of the present invention.
Figure 8:
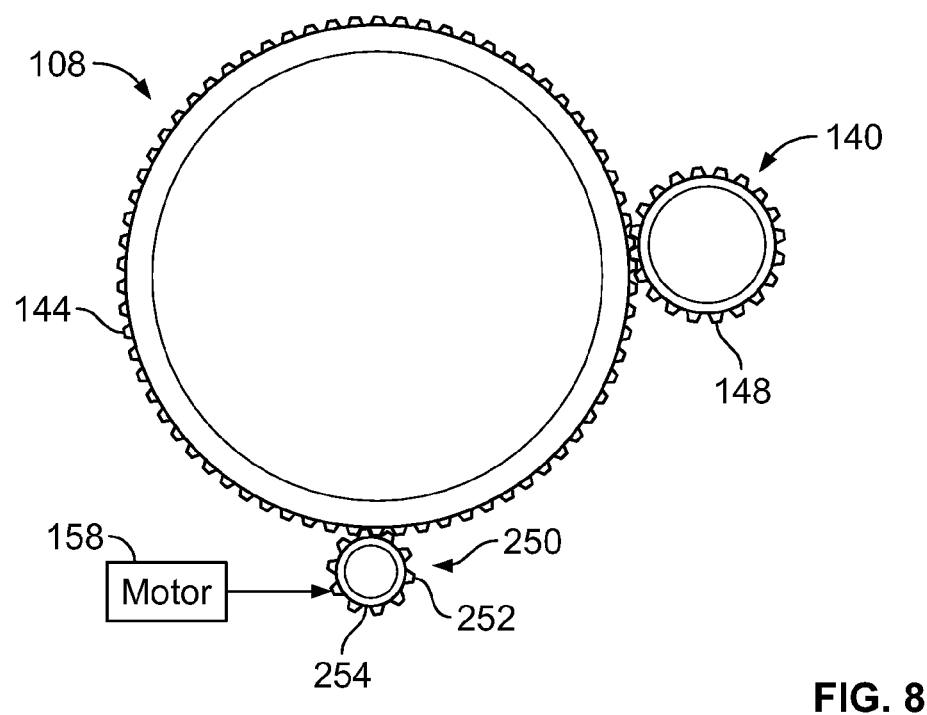
FIG. 8 illustrates another embodiment wherein the output from the motor drives the rotating portion in accordance with an embodiment of the present invention.
Figure 9:
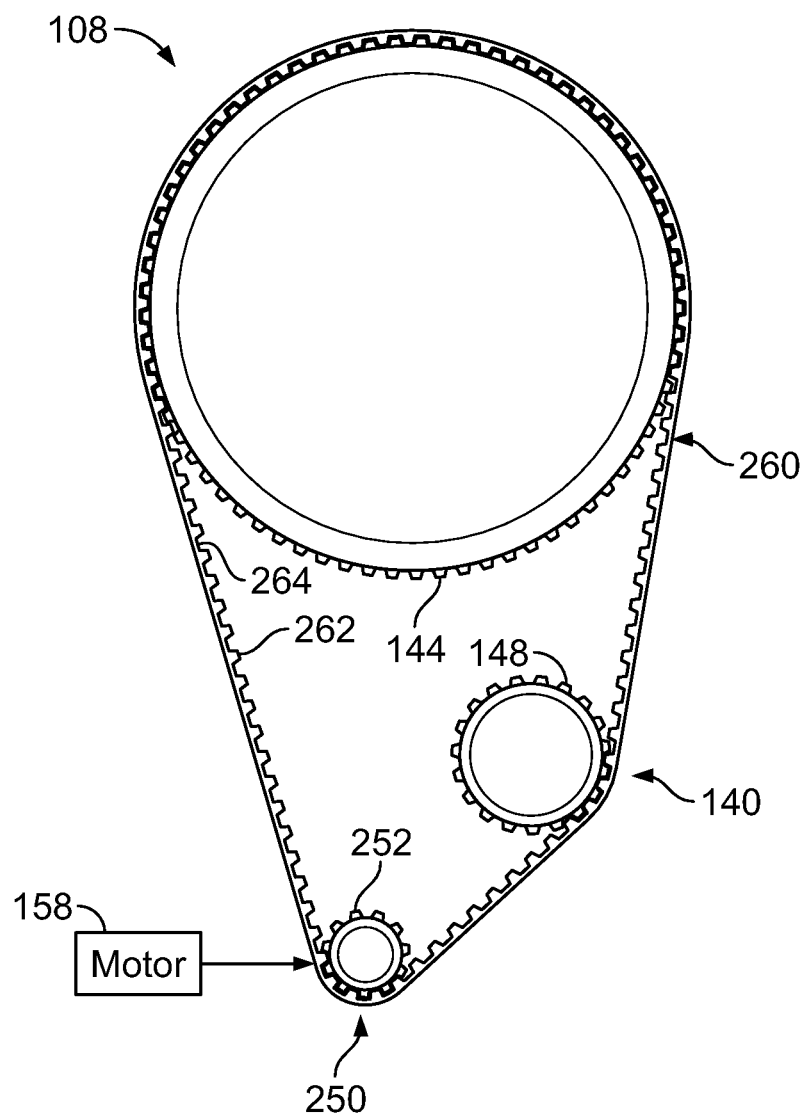
FIG. 9 illustrates another embodiment wherein a belt interconnects the rotating portion, the idler and a reduction gear in accordance with an embodiment of the present invention.

FIGS. 7-9 illustrate several configurations for driving the rotating portion 108 and the idler 140 to determine the absolute rotation. For clarity, the components illustrated in FIG. 3, such as the tilt sensor 156, the flags 150 and the sensors 152 and 154 are not shown. FIG. 7 illustrates an alternative embodiment wherein an output from the motor 158, such as reduction gear 250, drives the idler 140 and thus the rotating portion 108. The reduction gear 250 may have teeth 252 protruding from an outer edge 254 that engage without slippage with the teeth 148 of the idler 140. The teeth 148 of the idler 140 also engage with the teeth 144 of the rotating portion 108 as discussed above, resulting in a non-integer ratio of rotation between the idler 140 and the rotating portion 108.

FIG. 8 illustrates another embodiment wherein the output from the motor 158 and the reduction gear 250 drive the rotating portion 108. The teeth 252 of the reduction gear 250 engage the teeth 144 of the rotating portion 108 without slippage. Again, the teeth 148 of the idler 140 also engage with the teeth 144 of the rotating portion 108, and there is a non-integer ratio of rotation between the idler 140 and the rotating portion 108.

FIG. 9 illustrates yet another embodiment wherein a belt 260 interconnects the rotating portion 108, the idler 140 and the reduction gear 250. The belt 260 has teeth 262 that extend from an inner surface 264 to engage without slippage the teeth 144, 148 and 252 of the rotating portion 108, the idler 140 and the reduction gear 250, respectively. The position of the idler 140 may also be adjusted to adjust the tension of the belt 260.

Figure 10:
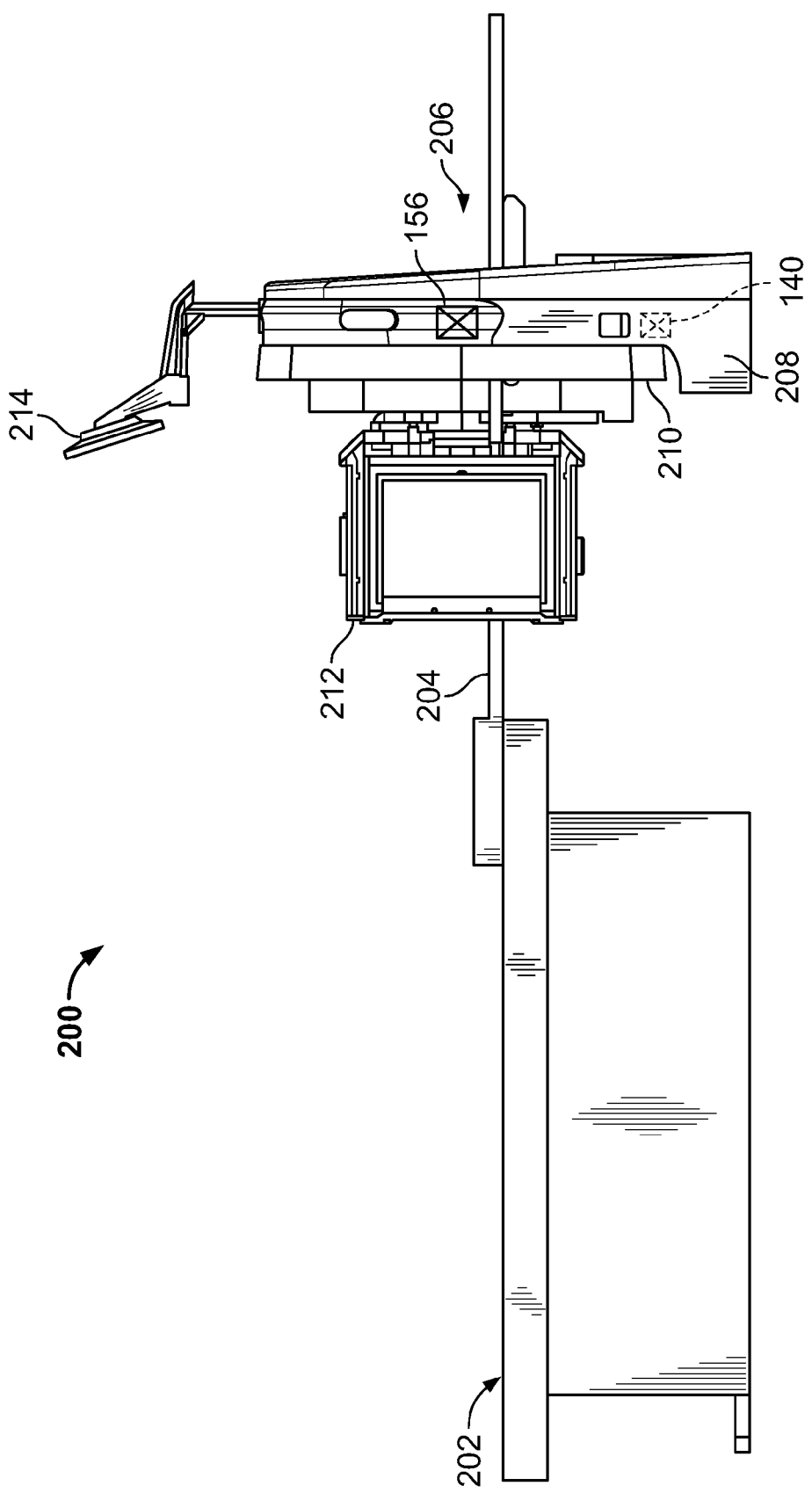
FIG. 10 illustrates an exemplary rotating imaging system that uses the idler and a tilt sensor to determine the absolute rotation of the rotating portion in accordance with an embodiment of the present invention.

FIG. 10 illustrates an exemplary rotating imaging system 200 that uses the idler 140 and the tilt sensor 156 to determine the absolute rotation of rotating portion 210. In this example, the system 200 is a nuclear medicine (NM) imaging system that may be used for nuclear single photon emission computed tomography (SPECT) imaging. The imaging system 200 has a table 202 with a pallet 204 that extends through an opening 206, similar to the opening 112 of FIG. 1. A stator 208 supports a rotor or rotating portion 210 and is mounted to the floor. Two imaging detectors are mounted on the rotating portion 210, although only one imaging detector 212 is shown. The idler 140 is mounted within the stator 208 and non-slippingly engages with the rotating portion 210. Any of the configurations as discussed in FIGS. 3 and 7-9 may be used. The tilt sensor 156 is also mounted on the rotating portion 210. Display 214 may display diagnostic images as well as information identifying the absolute rotation of the rotating portion 210 from column 196, the number and direction of revolutions, a warning that a rotation range or span is almost at a limit, and the like.

Figure 11:
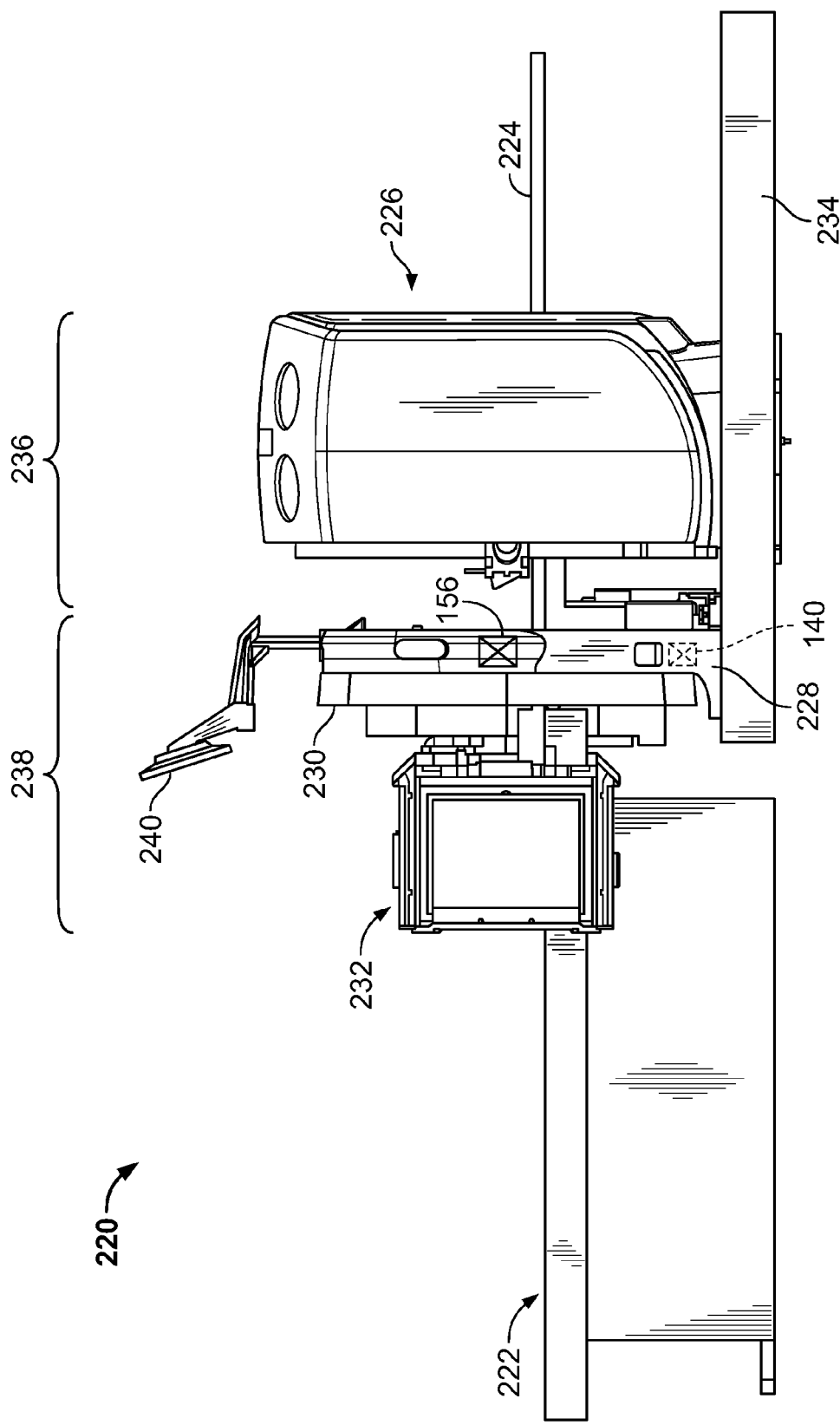
FIG. 11 illustrates another exemplary rotating imaging system that uses the idler and the tilt sensor to determine the absolute rotation of the rotating portion in accordance with an embodiment of the present invention.

FIG. 11 illustrates another exemplary rotating imaging system 220 that uses the idler 140 and the tilt sensor 156 to determine the absolute rotation of rotating portion 230. In this example, the system 220 is a multi-modality imaging system 220. The system 220 has an NM imaging system 238 capable of SPECT imaging and a computed tomography (CT) imaging system 236. Although the CT imaging system 236 is shown, it should be understood that other types of imaging systems may be paired with the NM imaging system 238 or included within the multi-modality rotating imaging system 220. Also, the CT imaging system 236 may be a full diagnostic CT system having detailed resolution or a lower resolution system used primarily for attenuation correction of the NM image data, anatomical registration and lower resolution imaging. As shown in FIG. 11, the imaging system 220 has a table 222 with a pallet 224 that extends through an opening 226. Also, a stator 228 supports a rotating portion 230 and at least one imaging detector 232. In this example, the stator 228 is mounted to at least one rail 234 and thus may be positioned with respect to the table 222. The CT imaging system 236 is also mounted to the at least one rail 234. It should be understood that at least one of the stator 228 and the CT imaging system 236 may instead be mounted to the floor.

The idler 140 is mounted within the stator 228 and non-slippingly engages with the rotating portion 230. The tilt sensor 156 is mounted on the rotating portion 230. As discussed in the system 200 of FIG. 10, any of the configurations of FIGS. 3 and 7-9 may be used. Display 240 may display one or more of the absolute rotation of the rotating portion 230 with respect to the zero degree position from column 196, the number of revolutions in one direction and a warning indicating when the retractor 106 nears the end of travel in either of the CW or CCW directions, as well as diagnostic images.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A rotating imaging system, comprising:
    a gantry having an opening that extends along a central axis therethrough, the opening being configured to accommodate a patient for imaging;
    a rotating portion having a diameter and being configured to rotate in clockwise and counterclockwise directions about the central axis a total rotation range between first and second ends of travel, wherein the total rotation range is more than one revolution and less than a predetermined number of revolutions;
    an idler configured to rotate about an axis parallel to the central axis, the idler having a second diameter that is smaller than the diameter of the rotating portion, the rotating portion and the idler configured to engage with each other such that both rotate simultaneously;

at least one sensor configured to detect flags on the idler as the idler rotates;

a tilt sensor mounted to the rotating portion and configured to determine a rotation angle of the rotating portion within a range of one revolution, the tilt sensor rotating around the opening when the rotating portion is rotated; and a processor configured to determine an absolute rotation of the rotating portion based on at least (i) a signal from the at least one sensor and (ii) the rotation angle determined by the tilt sensor, the absolute rotation being within the total rotation range, wherein the processor is configured to prevent the rotating portion from moving beyond the first end of travel or the second end of travel to prevent damage to the system.

2. The system of claim 1, wherein a ratio of rotation between the rotating portion and the idler is a non-integer ratio.

3. The system of claim 1, wherein the system is one of a nuclear medicine imaging system and a multi-modality imaging system that comprises at least a nuclear medicine imaging system.

4. The system of claim 1, further comprising a display configured to display at least one of the absolute rotation, a number of revolutions of the rotating portion, a direction of rotation of the rotating portion, and a warning associated with an end of travel.

5. The system of claim 1, wherein the rotating portion and the idler comprise outer edges having teeth extending outwardly therefrom, the teeth of the rotating portion engaging with the teeth of the idler.

6. The system of claim 1, wherein the flags are positioned equidistant around the idler.

7. The system of claim 1, further comprising:

a retractor mounted to the rotating portion and configured to rotate with the rotating portion, the retractor winding or unwinding as the rotating portion rotates, wherein the processor is configured to determine a warning condition when the rotation portion nears one of the first or second ends of travel in either travel.

8. The system of claim 1, further comprising a memory configured to store a look-up table that is configured to correlate the rotation angles to the absolute rotations based on the signal from the at least one sensor, the processor further configured to determine the absolute rotation based on the look-up table.

9. The system of claim 1, wherein said at least one sensor provides different indications to the processor when (a) the rotation angle has a predetermined value and the rotating portion is within one revolution and (b) the rotation angle has the same predetermined value and the rotating portion is within a different revolution.

10. The system of claim 1, wherein said at least one sensor comprises at least a first sensor and a second sensor that are each configured to provide a corresponding signal to the processor, the first and second sensors providing a different combination of corresponding signals to the processor when (a) the rotation angle has a predetermined value and the rotating portion is within one revolution and (b) the rotation angle has the same predetermined value and the rotating portion is within a different revolution.

11. The system of claim 1, wherein the processor is configured to determine a warning condition when the rotating portion nears the first end of travel or the second end of travel.

12. The system of claim 11, wherein the processor is configured to send instructions, after determining the warning condition, to at least one of (a) display a warning on a display, (b) provide a sound to alert an operator, (c) prevent further motion in a prohibited direction, (d) disable automatic motions, (e) activate a braking system, or (f) remove power that drives the rotating portion.

13. The system of claim 1, wherein the processor is configured to determine when the absolute rotation is near the first end of travel as the rotating portion rotates in a clockwise direction and when the absolute rotation is near the second end of travel as the rotating portion rotates in a counterclockwise direction.

14. The system of claim 1, wherein the flags comprise physical elements that rotate around the axis that is parallel to the central axis, the signal from the at least one sensor being indicative of a presence or absence of one or more flags.

15. The system of claim 1, wherein the total range is about 540 degrees, the absolute rotation indicating any number between 0 and about 540 degrees.

16. The method of claim 1, wherein the flags comprise physical elements that rotate around the axis that is parallel to the central axis, said at least one sensor comprising first and second sensors that are separated by a number of degrees, wherein adjacent flags are separated by a number of degrees that is different than the number of degrees that separates the first and second sensors.

17. A method for determining an absolute rotation of a rotating portion of an imaging system, the method comprising:

rotating a rotating portion and an idler simultaneously without slippage, the rotating portion and the idler configured to have a non-integer ratio of rotation with respect to each other, the rotating portion rotating about an opening of a gantry in clockwise and counterclockwise directions a total rotation range between first and second ends of travel, the total rotation range being more than one revolution and less than a predetermined number of revolutions;

detecting a flag on the idler as the idler rotates;

determining a rotation angle of the rotating portion using a tilt sensor that is mounted to the rotating portion, the rotation angle being within a range of one revolution, the tilt sensor rotating about the opening of the gantry;

determining an absolute rotation of the rotating portion based on at least the detection of the flag and the rotation angle, the absolute rotation being within the total rotation range;

determining a warning condition to prevent the rotating portion from moving beyond the first end of travel or the second end of travel to prevent damage to the system.

18. The method of claim 17, further comprising identifying a sensor that detected the flag, the absolute rotation being further determined based on the sensor.

19. The method of claim 17, wherein the detecting a flag further comprises at least one of detecting the presence of light with a sensor, detecting a magnetic field with a sensor, or detecting an ultrasonic response with a sensor.

20. A rotating imaging system, comprising:

a gantry having an opening that extends along a central axis therethrough, the opening being configured to accommodate a patient for imaging;

a rotating portion configured to rotate in clockwise and counterclockwise directions about the central axis a total rotation range between first and second ends of travel, wherein the total rotation range is more than one revolution and less than a predetermined number of revolutions;

an idler configured to rotate about an axis parallel to the central axis, the idler and the rotating portion having a non-integer ratio of rotation with respect to each other, the rotating portion and the idler configured to engage with each other such that both rotate simultaneously without slippage;

at least one sensor configured to provide a signal that is indicative of a rotational position of the idler;

a tilt sensor configured to determine a rotation angle of the rotating portion, the rotation angle being within a range of one revolution, the tilt sensor being located outside of the opening; and a processor configured to determine an absolute rotation of the rotating portion based on at least (i) the signal from the at least one sensor that is indicative of the rotational position of the idler and (ii) the rotation angle determined by the tilt sensor, wherein the processor is configured to determine when the absolute rotation is near the first end of travel and when the absolute rotation is near the second end of travel, wherein the processor is configured to prevent the rotating portion from moving beyond the first end of travel or the second end of travel to prevent damage to the system.

21. The system of claim 20, wherein the at least one sensor is configured to detect the presence of light generated by the at least one sensor, and wherein the flags are configured to interfere with the light when within a predetermined area of the at least one sensor.

* * * * *